(12) United States Patent
Klinder et al.

(10) Patent No.: US 11,413,006 B2
(45) Date of Patent: Aug. 16, 2022

(54) 3D IMAGE COMPOUNDING FOR ULTRASOUND FETAL IMAGING

(71) Applicant: KONINKLIJKE PHILIPS N.V., Eindhoven (NL)

(72) Inventors: Tobias Klinder, Eindhoven (NL); Cristian Lorenz, Eindhoven (NL); Irina Waechter-Stehle, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 824 days.

(21) Appl. No.: 16/093,175

(22) PCT Filed: Apr. 13, 2017

(86) PCT No.: PCT/EP2017/059018
§ 371 (c)(1),
(2) Date: Oct. 12, 2018

(87) PCT Pub. No.: WO2017/186518
PCT Pub. Date: Nov. 2, 2017

(65) Prior Publication Data
US 2019/0117186 A1    Apr. 25, 2019

(30) Foreign Application Priority Data

Apr. 26, 2016    (EP) .................................... 16167041

(51) Int. Cl.
*A61B 8/08* (2006.01)
*G01S 15/89* (2006.01)
(Continued)

(52) U.S. Cl.
CPC .......... *A61B 8/0866* (2013.01); *A61B 5/1071* (2013.01); *A61B 8/466* (2013.01);
(Continued)

(58) Field of Classification Search
CPC ..... A61B 8/0866; A61B 5/1071; A61B 8/466; A61B 8/467; A61B 8/483; A61B 8/5253;
(Continued)

(56) References Cited

U.S. PATENT DOCUMENTS

| 5,485,842 | A | 1/1996 | Quistgaard |
| 5,860,924 | A | 1/1999 | Quistgaard |

(Continued)

FOREIGN PATENT DOCUMENTS

| JP | 2011104137 A1 | 6/2011 |
| WO | 2007018338 A1 | 2/2007 |
| WO | 2016015994 A1 | 2/2016 |

OTHER PUBLICATIONS

Kim et al. "Programmable Ultrasound Imaging Multimedia Technologies: A Next-Generation Ultrasound Machine" IEEE Transactions On Information Technology in Biomedicine vol. 1, No. 1, Mar. 2, 1997.

(Continued)

*Primary Examiner* — Sanjay Cattungal

(57) ABSTRACT

The present invention provides an improved ultrasound imaging system arranged to evaluate a set of acquired 3D image data in order to provide a compounded 3D image of a fetus irrespective of its position and movement. This is achieved by providing an ultrasound imaging system comprising: an ultrasound probe having an ultrasound transducer array operable to acquire at different look directions a plurality of three dimensional (3D) ultrasound image frames of a volumetric region comprising a fetus; a compound image memory for storing the acquired plurality of the 3D ultrasound image frames and an articulated fetal model with a common fetal structure; an ultrasound image processor responsive to the plurality of 3D ultrasound image frames, said processor comprising a fetal segmentation unit arranged to segment each 3D image frame based on the articulated (Continued)

fetal model thereby providing a plurality of spatially related 3D images of the volumetric region; and an image quality analyzer coupled to the segmentation unit and arranged to determine, based on the articulated fetal model, an overall confidence value of the plurality of the 3D images, said image quality analyzer is further arranged to compare the overall confidence value with an image compounding threshold.

16 Claims, 7 Drawing Sheets

(51) Int. Cl.
- *G06T 7/33* (2017.01)
- *G01S 7/52* (2006.01)
- *G06T 7/149* (2017.01)
- *G06T 7/174* (2017.01)
- *A61B 5/107* (2006.01)
- *A61B 8/00* (2006.01)

(52) U.S. Cl.
CPC ............ *A61B 8/467* (2013.01); *A61B 8/483* (2013.01); *A61B 8/5253* (2013.01); *G01S 7/52098* (2013.01); *G01S 15/8993* (2013.01); *G01S 15/8995* (2013.01); *G06T 7/149* (2017.01); *G06T 7/174* (2017.01); *G06T 7/344* (2017.01); *A61B 8/5223* (2013.01); *A61B 8/5276* (2013.01); *G06T 2207/10132* (2013.01); *G06T 2207/10136* (2013.01); *G06T 2207/20124* (2013.01); *G06T 2207/30044* (2013.01); *G06T 2207/30196* (2013.01)

(58) Field of Classification Search
CPC . A61B 8/5223; A61B 8/5276; G01S 15/8993; G01S 15/8995; G01S 7/52098; G06T 7/344; G06T 7/149; G06T 7/174; G06T 2207/30196; G06T 2207/10136; G06T 2207/10132; G06T 2207/20124; G06T 2207/30044

See application file for complete search history.

(56) References Cited

U.S. PATENT DOCUMENTS

| | | | |
|---|---|---|---|
| 5,899,861 A | 5/1999 | Friemel | |
| 6,416,477 B1 | 7/2002 | Jago | |
| 7,033,320 B2 | 4/2006 | Von Behren et al. | |
| 7,507,204 B2* | 3/2009 | Shim | A61B 8/00 600/443 |
| 8,831,311 B2* | 9/2014 | Swamy | G16H 50/30 600/443 |
| 10,368,833 B2* | 8/2019 | Patruno | A61B 8/14 |
| 2005/0033173 A1 | 2/2005 | Von Behren et al. | |
| 2007/0167760 A1 | 7/2007 | Kim et al. | |
| 2007/0223794 A1* | 9/2007 | Preiss | G06T 7/33 382/128 |
| 2007/0255136 A1* | 11/2007 | Kristofferson | A61B 8/145 600/437 |
| 2009/0093717 A1* | 4/2009 | Carneiro | G06T 7/11 600/443 |
| 2009/0306503 A1* | 12/2009 | Srinivasan | A61B 8/461 600/441 |
| 2010/0277305 A1* | 11/2010 | Garner | A61B 8/4438 340/539.1 |
| 2013/0102857 A1* | 4/2013 | Wolfberg | A61B 5/344 600/382 |
| 2013/0150718 A1* | 6/2013 | Dixon | G01S 7/52061 600/443 |
| 2013/0150719 A1* | 6/2013 | Orderud | G06T 19/00 600/443 |
| 2013/0289407 A1 | 10/2013 | Lee | |

OTHER PUBLICATIONS

C. Wachinger, W. Wein, N. Navab "Three-Dimensional Ultrasound Mosaicing" Medical Image Computing and Computer-Assisted Intervention, MICCAI, 2007, Brisbane, Australia, Oct. 29-Nov. 2, 2007.

T. Klinder, H. Wendland, I. Wachter-Stehle, D. Roundhill, and C. Lorenz "Adaptation of an Articulated Fetal Skeleton Model to Three-Dimensional Fetal Image Data" SPIE Medical Imaging 2015.

* cited by examiner

3D IMAGE COMPOUNDING FOR ULTRASOUND FETAL IMAGING

This application is the U.S. National Phase application under 35 U.S.C. § 371 of International Application No. PCT/EP2017/059018 filed on Apr. 13, 2017, which claims the benefit of EP Application Serial No. 16167041, filed Apr. 26, 2016. These applications are hereby incorporated by reference herein.

FIELD OF THE INVENTION

The present invention relates to an ultrasound imaging apparatus for inspecting a volume of the subject comprising a fetus, in particular to an ultrasound imaging apparatus arranged combine three dimensional (3D) ultrasound image data into a spatially compounded 3D image of the fetus. The present invention further relates to a method for combining 3D ultrasound image data of the fetus into a spatially compounded 3D image of the fetus.

BACKGROUND OF THE INVENTION

Fetal imaging is currently developing towards 3D ultrasound imaging. In the later gestational ages of fetus a field of view of the ultrasound transducer is no longer covering the full fetus as illustrated in FIG. 1. As a result, different portions of the body are acquired separately (e.g., brain, abdomen, femurs, see FIG. 3). In order to get one compounded view image stitching or mosaicking is known technique extensively used for 2D imaging (e.g., panorama viewing for camera pictures).

One major difference for image compounding is the fact that in the case of fetal imaging not a static scene is imaged but the fetus, which is (sometimes even extensively) moving between two acquisitions. This does not only hamper image compounding (image stitching), but can also create scenarios where mosaicking is no longer feasible or plausible (especially in case of a large motion of the extremities). This situation is illustrated in FIG. 4; wherein in FIG. 4A example, the fetal arms are positioned in front of the belly, while in FIG. 4B in example the arms are positioned in front of the fetal face. In this situation a standard image compounding by spatially stitching images acquired at different orientations will not provide a good quality compounded image.

SUMMARY OF THE INVENTION

It is therefore an object of present invention to provide an improved ultrasound imaging system arranged to evaluate a set of acquired 3D image data in order to provide a compounded 3D image of a fetus irrespective of its position and movement.

According to one aspect of the present invention, an ultrasound imaging system for producing a spatially compounded image of a fetus comprising:

an input for receiving a plurality of three dimensional (3D) ultrasound image frames of a volumetric region comprising the fetus, wherein each 3D ultrasound image frame is acquired by an ultrasound probe at a different look direction with respect to the fetus; and an ultrasound image processor responsive to the plurality of 3D ultrasound image frames, said processor arranged to:

store the acquired plurality of 3D ultrasound image frames and an articulated fetal model, wherein the articulated fetal model includes a common fetal structure and at least one joint-limb relationship, segment each 3D image frame based on the articulated fetal model, wherein the ultrasound image processor if further arranged to adapt the articulated fetal model applied to a 3D image frame, when a variation of the common fetal structure compared to another 3D image frame of the plurality is detected, provide a plurality of 3D images of the volumetric region with an identified relative orientation of the fetus with respect to the look direction of the segmented image; and analyze coupled to the segmentation unit and arranged to determine, based on the articulated fetal model, an overall confidence value of the plurality of the 3D images, said image quality analyzer is further arranged to compare the overall confidence value with an image compounding threshold.

The ultrasound system of the present invention allows evaluating the overall quality of the 3D images of the fetus acquired for the given volumetric region. This evaluation is done by determining an overall confidence value of the plurality of the 3D images based on the incorporated knowledge of an articulated position taken by the fetus during each 3D frame acquisition. While segmenting each ultrasound 3D frame a variation of the common fetal structure in a given 3D frame compared to another 3D image frames can be detected, in the case the ultrasound imaging system allows adapting the articulated fetal model applied to the given 3D image frame. In some cases the relative orientation of the fetus may vary substantially between opposite directions from one 3D image to another. For such cases it may better to reacquire some 3D image frames than giving a user a low quality compounded image. Therefore, the image quality analyser of the system is arranged to compare the determined overall confidence value with an image compounding threshold, above which a spatially compounded 3D image of the fetus would provide an improved visualization of the volumetric region. The system of the present invention may further include a user feedback capability informing the user, when the overall confidence value is below the image compounding threshold. This provides user with an additional flexibility of either performing an additional 3D image frames acquisition or continue with the rest of the selected diagnostic protocol, if time is a limiting factor.

The benefit of the present ultrasound system lies in using the articulated fetal model, which includes the common fetal structure and at least one joint-limb relationship, in combination with the model's subsequent adaptation during the segmentation process of the 3D image frames. This permits the ultrasound system to automatically assess an extent of a fetal pose change, which might have occurred during the acquisition of the plurality of three dimensional (3D) ultrasound image frames. If the common fetal structure in between the subsequently acquired frames varies substantially such that the model's adaptation causes a reduction of the overall confidence value of the plurality of the 3D images the user may be notified.

According to another aspect of the present invention the ultrasound imaging system further comprises a spatial image combiner arranged to provide, when the overall confidence value is above the image compounding threshold, a spatially compounded 3D image of the fetus, wherein different regions of said compounded 3D image are formed based on contributions from the plurality of 3D images.

According to a further aspect of the present invention, a medical imaging method for inspecting a volumetric region comprising fetus is provided comprising the steps of:

receiving a plurality of three dimensional (3D) ultrasound image frames of a volumetric region with the fetus, wherein each 3D ultrasound image frame is acquired at a different look direction with respect to the fetus, from an ultrasound probe, storing the acquired plurality of the 3D ultrasound image frames and an articulated fetal model with a common fetal structure, wherein the articulated fetal model includes a common fetal structure and at least one joint-limb relationship;

segmenting each 3D image frame based on the articulated fetal model;

adapting the articulated fetal model applied to a 3D image frame, when a variation of the common fetal structure compared to another 3D image frame of the plurality is detected;

providing a plurality of 3D images of the volumetric region with an identified relative orientation of the fetus with respect to the look direction of the segmented image and providing a spatially compounded 3D image of the fetus, wherein different regions of said compounded 3D image are formed based on contributions from the plurality of 3D images.

Preferred embodiments of the invention are defined in the dependent claims. It shall be understood that the claimed method has similar and/or identical preferred embodiments as the claimed device and as defined in the dependent claims.

The present invention further provides a novel way of generating a compounded 3D image of the fetus with improved image quality. The suggested way is robust towards fetus movements in between the acquired 3D image frames. The ultrasound system in accordance to the present invention allows compensating even for an extreme fetal movement, wherein variable parts of a fetal body may change their relative position with respect to the body, and provides an improved compounded 3D image of this fetus. This is achieved by the incorporating a knowledge on an articulated position taken by the fetus during each 3D frame acquisition. The articulated fetal model includes the common fetal structure and at least one joint-limb relationship, this way a specific to the fetus set of movements and their effect on the overall image quality can be assessed. These movements can include relatively small pose variations such as join-limb movements or change of the fetus orientation to an opposite direction. This knowledge enables the ultrasound system of the present invention to provide a plurality of 3D ultrasound images, wherein relative orientation of the fetus with respect to the look direction is identified for each 3D frame. Further, once the overall confidence value is above the image compounding threshold, the system is arranged to generate the spatially compounded 3D image, wherein different regions are formed based on contributions from the plurality of 3D ultrasound images. Consequently, a high quality compounded ultrasound image of the fetus can be provided in real time with low technical effort, so that the acquiring of the ultrasound image is more comfortable and the quality is increased.

In a further embodiment of the present invention the overall confidence value includes a spatial combination of confidence values, each confidence value corresponding to a 3D image from the plurality of the 3D images and the spatial image combiner arranged to provide the spatially compounded 3D image of the fetus, wherein different regions of said compounded 3D image are weighted on the basis of the different confidence values of the 3D images from the plurality of 3D images.

In this embodiment the system can determine confidence values for different 3D frames with respect to the defined common fetal structure. The image quality analyzer may further analyze an image quality of each acquired 3D frame and determine a corresponding confidence value based on this analyses. In this embodiment the system provides the compounded 3D image, wherein each contributing to it 3D image is weighted in accordance to its confidence value. Hence, a wrong clinical diagnosis due to artefacts can be reduced and the reliability of the fetal ultrasound imaging is increased.

In another embodiment, the plurality of 3D ultrasound image frames further comprises an assembly of partial 3D image frames, each partial 3D image frame corresponding to the volumetric region, which includes a portion of the fetus.

This embodiment takes into account a possibility that not in all acquired 3D ultrasound frames the fetus will be fully visualized. These partial 3D image frames would include only a portion of the fetus.

In yet another embodiment, the ultrasound image processor comprises a fetal segmentation unit arranged to adapt the articulated fetal model applied to each of the partial 3D image frames based on the portion of the fetus included in each frame.

This embodiment provides a further improvement of the compounded 3D image quality by adapting the articulated model, used for the segmentation, in accordance to the portion of the fetus anatomy visualized in each of the partial frames. This step allows to determine more precisely a confidence value corresponding to the respective 3D image originating from the partial 3D image frame. The adaptation of the articulated fetal model may, for example, include varying a joint-limb relationship of the common fetal structure.

In yet another embodiment, the system further comprises a user interface coupled to the ultrasound image processor and responsive to user manual identification of at least one anchor landmark in the 3D image frame, said user interface is arranged to provide the identified location of the anchor landmark, such as joint pivot, within the 3D image frame as an input for the adaptation of the articulated fetal model.

This embodiment enables the system to use user's input for the adaptation of the articulated fetal model. The user can identify an anchor landmark within the 3D image frame. A possibility of the manual input may facilitate a more precise and quick adaptation of the articulated fetal model.

In a yet another embodiment, the ultrasound image processor comprises an image quality analyzer arranged to determine confidence values of the 3D images, which originate from 3D frames segmented with the same fetal articulation, being relatively higher with respect to confidence values corresponding to 3D images, which originate from 3D frames segmented with a different fetal articulation.

The improved compounded 3D image can be achieved by combining the 3D images with the same fetal pose (fetus image with the same articulation). Thus, an advantage of this embodiment is that 3D images with a fetal structure being different from the given fetal structure (due to the fetus movement in between the frames acquisition) used for the compounded 3D image can be identified and given low confidence values. The weight of the 3D images having these relatively low confidence values will be reduced accordingly in the compounded 3D image.

In another embodiment, the system further comprises a display operated to display the compounded 3D image and the reference orientation model of the fetus with respect to the volumetric region.

This embodiment improves visualization of the compounded 3D image by displaying a reference orientation model of the fetus as well. The reference orientation model can be either shown in a separate window next the compounded 3D image; or interposed on to the compounded 3D image. This way the user may get a better spatial feeling of the fetal position and its orientation with respect to the probe.

In another embodiment, the system further comprises a user interface coupled to the ultrasound image processor, said user interface arranged to enable the user to perform biometry measurements of the fetus based on displayed the spatially compounded 3D image.

The improved quality compounded 3D image provided in accordance to the present invention enables the system to provide the user with possibility to perform a more precise biometry measurements of the fetus used in obstetric ultrasound.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
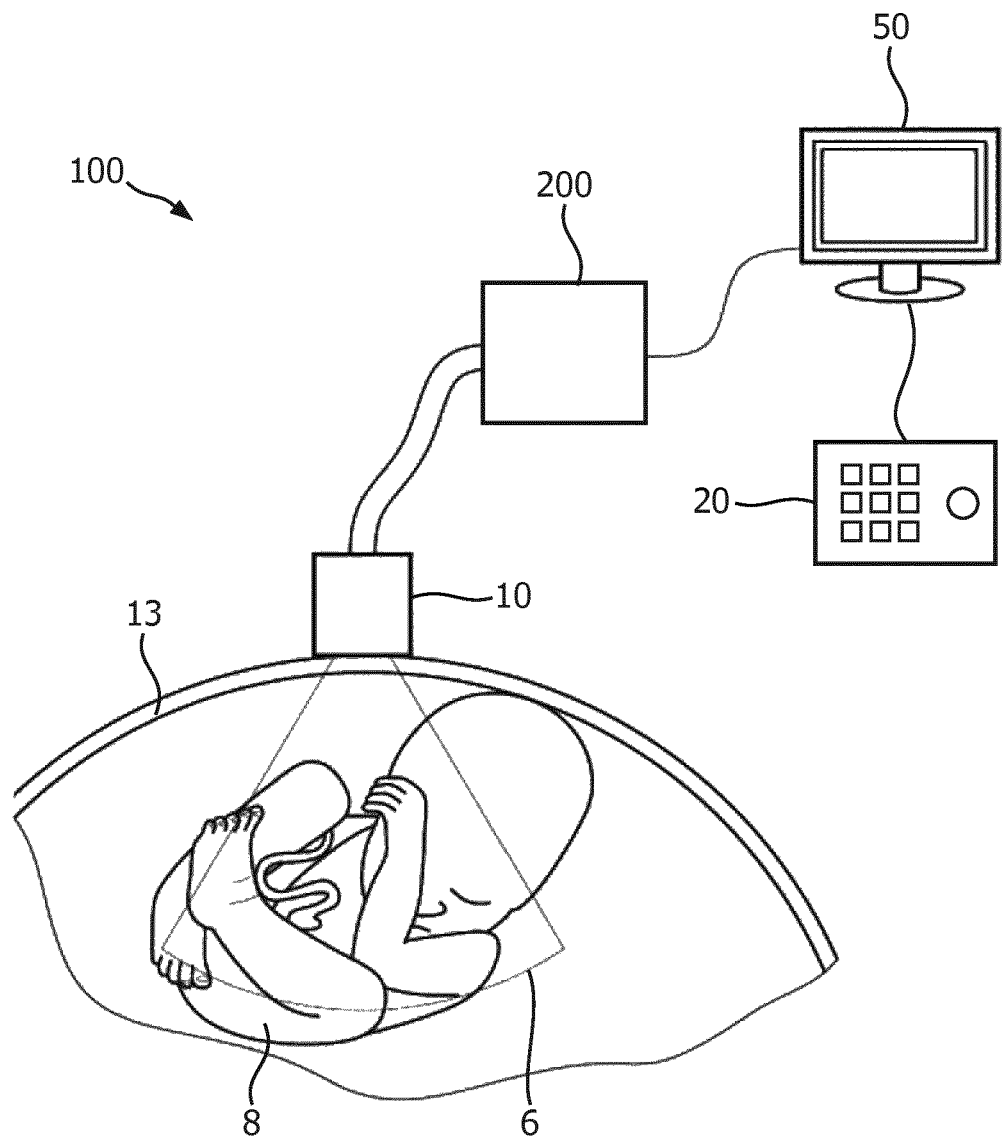
FIG. 1 shows a schematic representation of an ultrasound imaging system in use to scan a volume of a patient's body including a fetus.

FIG. 1 shows a schematic illustration of an ultrasound imaging system according to an embodiment generally denoted by 100. The ultrasound imaging system 100 is applied to inspect a volumetric region of an anatomical site, in particular an anatomical site of a patient 13 including a fetus 8. The ultrasound imaging system 100 comprises an ultrasound probe 10 having at least one transducer array having a multitude of transducer elements for transmitting and/or receiving ultrasound waves. The transducer elements are preferably arranged in a two-dimensional (2D) array, which is constructed to electronically steer ultrasound beams within the volumetric region such that a three-dimensional ultrasound image frame of said region is provided. Alternatively, the array may be a one-dimensional array (1D) constructed to be mechanically steered through the volumetric region in order to provide a three-dimensional ultrasound image frame. The probe 10 is adapted to transmit ultrasound waves in a particular direction and to receive ultrasound waves from a particular direction which forms a field of view 6 for a given 3D image frame of the ultrasound probe 10.

In the embodiment shown in FIG. 1, the patient 13 is a pregnant person, wherein an anatomical object to be inspected is a fetus 8, part of which is disposed in the field of view 6.

As fetus represents a non-static object its position can vary from one 3D image frame to another. In addition, due to the physics of the ultrasound propagation in tissue, certain regions in the field of view 6 may not reflect the anatomical structures of the fetus 8 since some areas may be shadowed or masked by other anatomical structures within the ultrasound propagation path. Further, at later gestational ages of fetus the field of view 6 of the ultrasound transducer is no longer including an entire fetal body. As described in the following, the ultrasound system 100 in accordance to the present invention can evaluate an overall quality of the 3D image frames acquired for a given diagnostic protocol. Once the evaluated quality, expressed by an overall confidence value, is sufficient for generation of a compounded 3D image of the fetus, the ultrasound system of the present invention is arranged to produce a compounded 3D ultrasound image by combining 3D ultrasound images originating from a plurality of 3D image frames acquired at different viewing directions so that the amount of image quality defects can be reduced.

It is common in obstetric examination that ultrasound data acquired by the probe 10 with different probe positions or angles of steered beams result in ultrasound image frames having a variation in their quality, thus representing different confidence levels in diagnosing. The ultrasound imaging system 100 may either comprises the probe or an input wherein the ultrasound image data acquired by the probe 10 are received. The system may further comprise an ultrasound imaging apparatus 200 such as a control unit, which controls the provision of an ultrasound image via the ultrasound system 100. As will be explained further below, the ultrasound imaging apparatus 200 may receive ultrasound image data through the input from the transducer array of the ultrasound probe 10 and provides a compounded three-dimensional (3D) ultrasound image derived from the different ultrasound data sets of the fetus 8.

The ultrasound imaging system 100 may further comprise a display 50 for displaying the ultrasound image received from the ultrasound imaging apparatus 200. Still further, a user interface 20 may be provided that may comprise keys or a keyboard and inputting devices and may be connected to the display 50 or directly to the ultrasound imaging apparatus 200.

Figure 2:
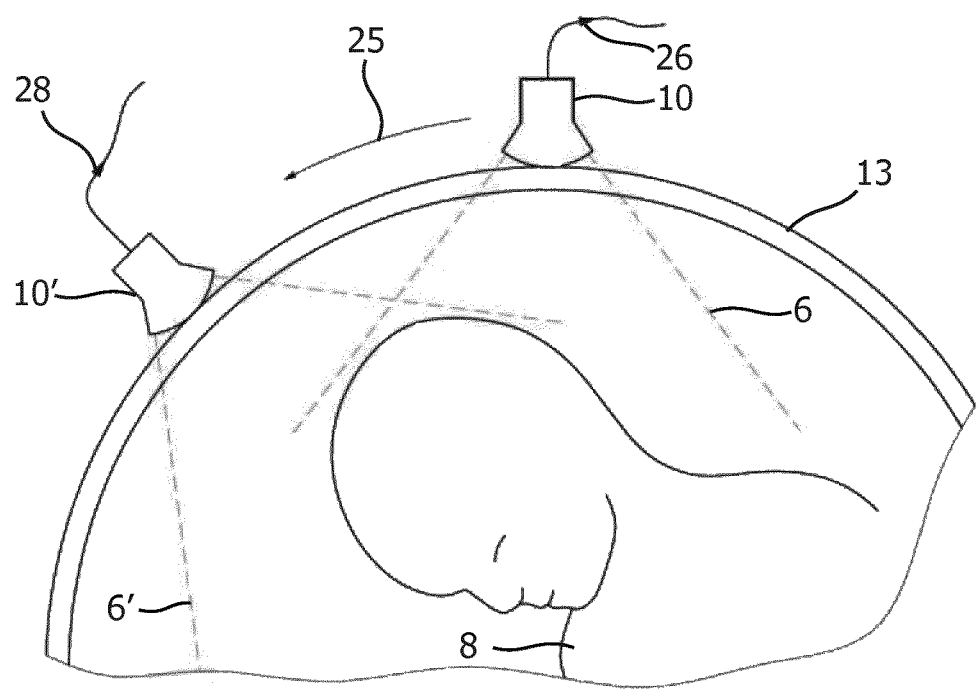
FIG. 2 shows a schematic illustration of different ultrasound frames of a volumetric region comprising the fetus acquired in different look (viewing) directions.

In FIG. 2 a schematic perspective diagram is shown for explaining an acquisition of the ultrasound image frames from different viewing directions with respect to the volumetric region comprising the fetus 8. The probe 10 is shifted around the patient's body 13 as indicated by an arrow 25 in order to acquire different ultrasound frames 26, 28 from the different viewing directions so that the fetus 8 is differently oriented within the field of view 6, 6'. These 3D frames may capture a different pose of the fetus, in case the fetus moved during the probe's shift, and the frames may also comprise different regions shadowed or obscured due to the propagation direction of the ultrasound waves can be reduced. In alternative workflow embodiment an acquisition of the image plurality at different look direction with respect to the fetus may be achieved by means of ultrasound beams steering (either electronical or mechanical) performed at the fixed probe's position with respect to the patient's body.

In order to provide a high quality ultrasound image, the ultrasound imaging apparatus 200 is arranged to combine the different ultrasound frames 26, 28 of the different look (viewing) directions to a compounded 3D ultrasound image on the basis of different spatial references identified in the field of view 6, 6'. The spatial references are identified on the basis of segmented anatomical structures of the fetus 8 as described in detail in the following.

Figure 3:
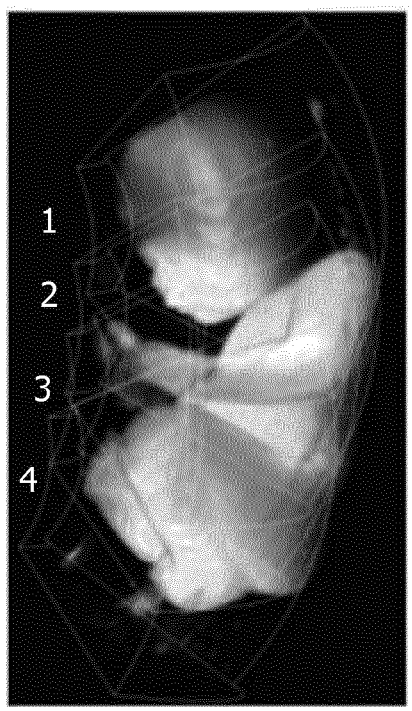
FIG. 3 shows a schematic illustration of different partial 3D frames of a volumetric region comprising the fetus acquired in different look (viewing) directions.

Referring to FIG. 3, the ultrasound probe 10 can acquire a plurality of 3D ultrasound image frames denoted as 1, 2, 3 and 4 and corresponding to a different look direction with respect to fetus. All frames or some (an assembly) of these frames may be partial 3D image frames, wherein each of the partial frames includes a portion of the fetus as shown in FIG. 3. These partial 3D image frames comprise image data of a specific anatomy of the fetus, which is included in the field of view for the given look direction. This situation may often occur in later gestational ages, when the fetal size may be larger than the field of view of the probe.

Figure 4A:
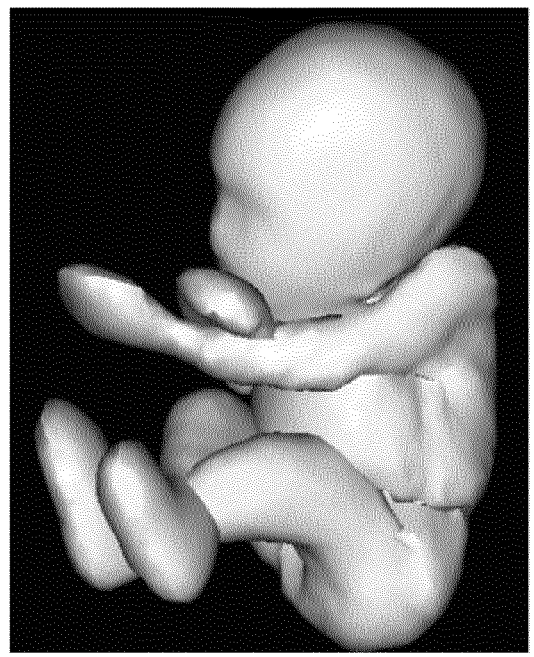
FIGS. 4A-B show different articulated structures of the fetus.
Figure 4B:
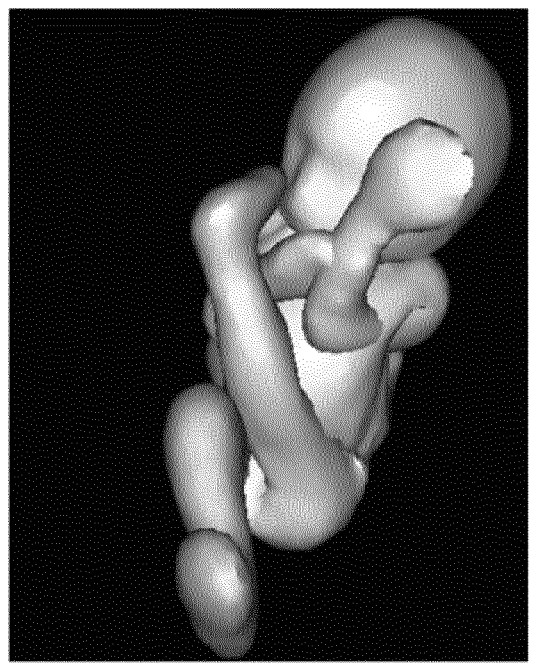

The 3D image frames may vary in their image quality dependent on the part of the fetal anatomy visualized by the field of view of the given frame. In addition, a fetus pose (articulation) can change from frame to frame as illustrated in FIGS. 4A-B. The described below in detail in FIG. 5 the ultrasound system of the present invention allows to generate a compounded 3D image of the fetus with improved image quality, which is robust towards fetus movements in between the acquired 3D image frames. The ultrasound system 100 comprises a compound image memory 32 arranged to store data of the acquired plurality of the 3D ultrasound image frames and an articulated fetal model with a common fetal structure.

Figure 6:
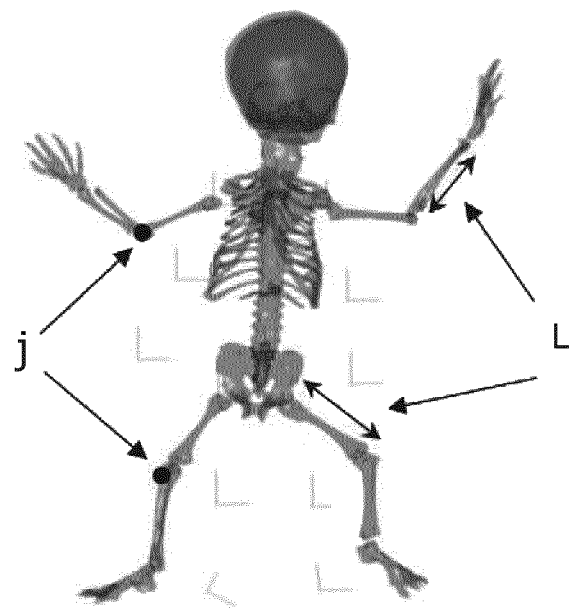
FIG. 6 illustrates a representation of an articulated model of the fetus.

The articulated fetal model takes into account the variability in overall orientation and articulated constellation of the fetal body. This model covers the most important articulation of the fetal skeletal anatomy and defines the degrees of freedom per articulation including range of motion (min/max angles). The implementation of the model is commonly done using joint (j)-limb (L)-relationships. By defining the common fetal structure a three-dimensional data set comprising fetus can be segmented. The idea is illustrated in FIG. 6 on a synthetic example. The articulated model gives for each joint the respective articulation parameters (rotation point and angles) and thus defines the overall constellation. In this model following assumptions may be used. Each limb carries a shape, each limb can be saleable, can have a parent joint, can have a list of child-joints. Each joint can be a hinge or a ball joint, has a static limb (with respect to this joint), has a flexible limb. Thus, articulation can be defined by a rotation point, rotation axes and min/max of angulation values. The fetus position is given by the coordinate systems which define the location and rotation parameters of the respective joints. Based on this input, the actual fetus pose position (articulation) in the medical image can be determined using inverse kinematics to fit the desired position. When solving the inverse problem the degrees of freedom are considered per joint.

Figure 5:
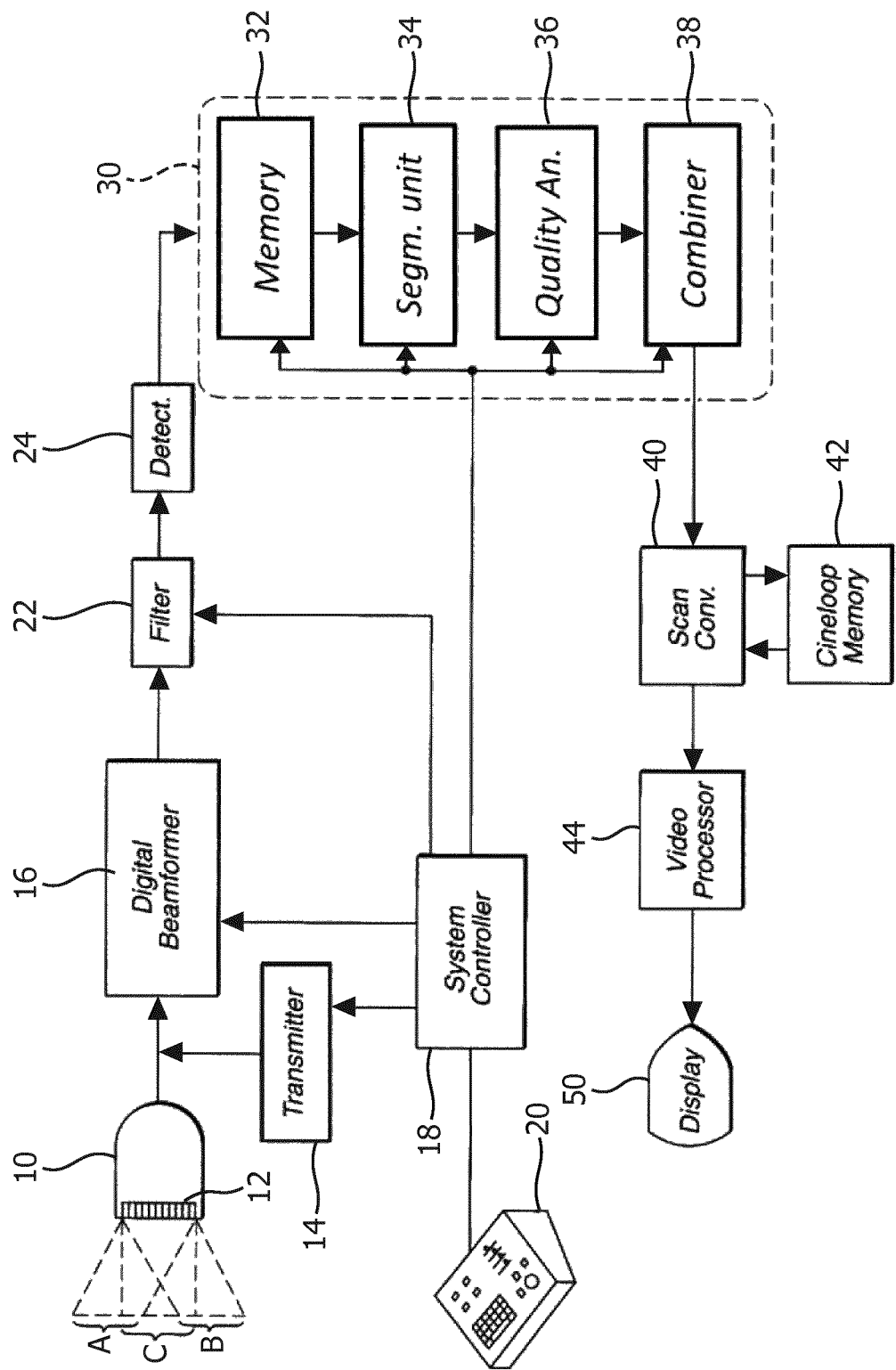
FIG. 5 illustrates in block diagram form an ultrasonic diagnostic imaging system constructed in accordance with the principles of the present invention.

FIG. 5 shows a detailed schematic block diagram of the ultrasound imaging system 100 constructed in accordance with the present invention. The probe 10 including the transducer array 12 transmits beams at different angles over an image field denoted by the dashed rectangle and parallelograms. In this example, three groups of scanlines forming a plurality of image frames are indicated in the drawing, labeled A, B, and C with each group being steered at a different angle relative to the probe. In contrast to the example illustrated in FIG. 3, wherein the 3D frames denoted as 1, 2, 3 and 4 are acquired by shifting the probe 10 (similar to the case in FIG. 2), the 3D image frames labeled as A, B and C in FIG. 5 are acquired by electronically steered ultrasound beams. The transmission of the beams is controlled by a transmitter 14 which controls the phasing and time of actuation of each of the elements of the array transducer so as to transmit each beam from a predetermined origin along the array and at a predetermined angle. The echoes returned from along each scanline are received by the elements of the array, digitized as by analog to digital conversion, and coupled to a digital beamformer 16. The digital beamformer delays and sums the echoes from the array elements to form a sequence of focused, coherent digital echo samples along each scanline. The transmitter 14 and beamformer 16 are operated under control of a system controller 18, which in turn is responsive to the settings of controls on the user interface 20 operated by the user of the ultrasound system. The system controller controls the transmitter to transmit the desired number of scanline groups at the desired angles, transmit energies and frequencies. The system controller also controls the digital beamformer to properly delay and combine the received echo signals for the apertures and image depths used. The scanline echo signals are filtered by a programmable digital filter 22, which defines the band of frequencies of interest. When imaging harmonic contrast agents or performing tissue harmonic imaging the passband of the filter 22 is set to pass harmonics of the transmit band. The filtered signals are then detected by a detector 24. In a preferred embodiment the filter and detector include multiple filters and detectors so that the received signals may be separated into multiple passbands, individually detected and recombined to reduce image speckle by frequency compounding. For B mode imaging the detector 24 will perform amplitude detection of the echo signal envelope. For Doppler imaging ensembles of echoes are assembled for each point in the image and are Doppler processed to estimate the Doppler shift or Doppler power intensity.

Figure 7:
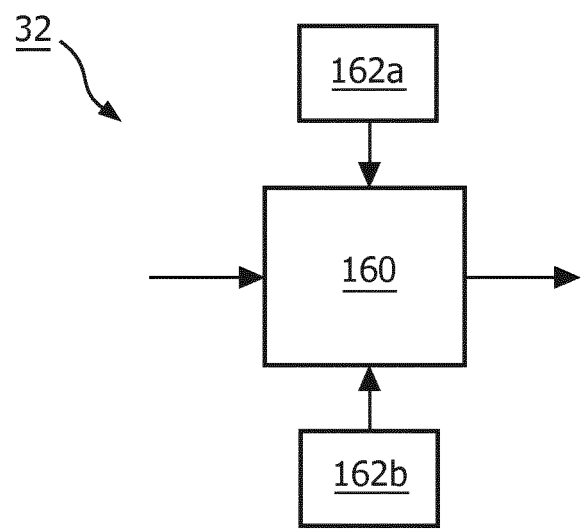
FIG. 7 illustrates a dual ported memory used for acquired 3D image frame storage in an implementation of the present invention.

In accordance with the principles of the present invention the digital echo signals are processed by spatial compounding in an ultrasound image processor 30. In the embodiment shown in FIG. 5 the ultrasound image processor comprises the compound image memory 32 unit. In other system's realization this unit can be also located outside of the processor 30. The compound image memory 32 is a 3D frame storage buffer and can be implemented as a dual port memory 160 which can be written to and read from simultaneously (FIG. 7). The use of such a R/W memory enables the new 3D ultrasound image frames being acquired by the transducer array and beamformer to be written into one area of the R/W memory while the data of other 3D image frames previously stored in the memory is read out and analyzed. The writing of new slice image data into the memory 160 is controlled by a write address controller 162a while the reading of slice image data from other locations in the memory is under the control of a read address controller 162b. This embodiment illustrates how a real time image analyses and compounding may be performed. The compound image memory unit 32 further stores the articulated fetal model with the defined common fetal structure.

The ultrasound image processor may comprise a segmentation unit 34 arranged to segment each 3D image frame based on the articulated fetal model stored in the memory unit 32. The segmentation unit 34 model thereby provides a plurality of 3D images originating from the plurality of 3D frames (A,B and C as illustrated in FIG. 5 or 1, 2, 3, 4 as illustrated in FIG. 3) of the volumetric region, wherein a relative orientation of the fetus with respect to the look direction is identified for each 3D image. The relative orientation of the fetus linked to the 3D image gives a spatial relationship between the acquired 3D frames. The segmentation unit 34 further allows to adapt the articulated fetal model applied to different 3D images, when a variation of the common fetal structure compared to another 3D image frame of the plurality is detected. The articulated fetal model includes the common fetal structure and at least one joint-limb relationship, this way a specific to the fetus set of movements and their effect on the overall image quality can be assessed. These movements can include relatively small pose variations such as join-limb movements or change of the fetus orientation to an opposite direction.

This plurality of the spatially related 3D images may be further processed by an image quality analyzer 34, which is arranged to determine an overall confidence value of the plurality of the 3D images. Image quality of the acquired 3D frame may vary from one look to another. The ultrasound image processor 30 enables the ultrasound system 100 to automatically assess an extent of a fetal pose change, which might have occurred during the acquisition of the plurality of three dimensional (3D) ultrasound image frames. If the common fetal structure in between the subsequently acquired frames varies substantially such that the model's adaptation causes a reduction of the overall confidence value of the plurality of the 3D images the user may be notified. Some of the anatomical features of the fetus may be less pronounced for the given 3D frame due to the variation in the transmitted and reflected echo signals. Therefore, depending on a selected by user diagnostic protocol directed to a specific fetal anatomy observation (for example, neurosonogram), the quality analyzer 34 may denote a relatively low confidence values to those 3D images, wherein the specific anatomy is not fully visualized. While the 3D images corresponding to the frames with the specific anatomy being well pronounced may be denoted relatively high confidence values. Compared to the prior art systems the quality analyses is improved by implementing the fetal articulation knowledge into the segmentation step. Further, the quality analyzer 34 is also arranged to identify a potential fetal movement, which may occur in between or during the 3D frame acquisition. If a fetal structure for the given 3D image frame changes compared to the common fetal structure identified for the rest of the plurality of the 3D image frames, the quality analyzer 34 denotes the relatively low confidence value to the 3D image, wherein the movement was identified. Thus, 3D images, which originate from 3D frames segmented with the same fetal articulation, have relatively higher confidence values compared to 3D images, which originate from 3D frames segmented with a different fetal articulation. The overall confidence value of the plurality of the 3D images determined by the analyzer 34 is based on a spatial combination of confidence values originating from the 3D image frames, wherein each value corresponds to a 3D frame from the plurality of the 3D images. In order to obtain the overall confidence values, these confidence values may be either summed or averaged through the volumetric region. The image quality analyzer 34 is further arranged to compare the determined overall confidence value to an image compounding threshold. This threshold can reflect a lower limit below which a spatially compounded 3D image would not provide an improved quality for a diagnosis. The threshold can be defined by the selected diagnostic protocol and image quality requirements set for an observation of the specific fetal anatomy performed by said protocol (anatomical features expected to be visualized during the examination). Therefore, the overall confidence value provided by the ultrasound image processor may be different for the same plurality of 3D image frames, when different diagnostic protocols are selected. The system of the present invention has an additional flexibility in the image quality assessment, wherein a diagnostic purpose of the acquired plurality of images is automatically taken into account. While for some diagnostic protocols an occurrence of the fetus movement during the acquisition may affect a quality of the diagnosis; for other diagnostic protocols the same movement would not have a substantial effect.

When the overall confidence value is determined to be below the image compounding threshold, the ultrasound system of the present invention is arranged to provide the user with a feedback indicating that the quality of the acquired 3D frames is not sufficient for the 3D image compounding. At this stage the user can decide whether to perform 3D frames acquisitions again or to proceed with a next in the protocol. After quality analyses the spatially 3D images are compounded by a spatial image combiner 38. Combining may comprise summation, averaging, peak detection, or other combinational means. The combiner is arranged to provide spatially compounded 3D image of the fetus, wherein different regions of said compounded 3D image are formed based on contributions from the plurality of 3D images. The images being combined may also be weighted based on their confidence values prior to combining in this step of the process. The 3D images with the fetal structure being different from the given fetal structure and/or 3D images with the desired fetal anatomy being less pronounced will have low confidence values. The weight of these 3D images may be reduced accordingly in the compounded 3D image. Thus, providing an improved quality compounded 3D image of the fetus. This would result in a wrong clinical diagnosis due to artefacts to be reduced and the reliability of the fetal ultrasound imaging to be increased.

Finally, post processing is performed by the processor. The processor normalizes the combined values to a display range of values. This processing can be most easily implemented by look-up tables and can simultaneously perform compression and mapping of the range of compounded values to a range of values suitable for display of the compounded image. The compounding process may be performed in estimate data space or in display pixel space. Additionally to post-processing raylines can be mathematically projected through the multiple 3D images in the manner of raycasting for volume rendering. The spatially compounded 3D image of the present invention provides an improved image quality data suitable for volume rendering of the fetus. In a preferred embodiment scan conversion is done following the compounding process by a scan converter 40. The compound images may be stored in a Cineloop® memory 42 in either estimate or display pixel form. If stored in estimate form the images may be scan converted when replayed from the Cineloop memory for display. The scan converter and Cineloop memory may also be used to render three dimensional presentations of the spatially compounded images as described in U.S. Pat. Nos. 5,485,842 and 5,860,924. Following scan conversion the spatially compounded images are processed for display by a video processor 44 and displayed on an image display 50.

An improvement in the quality of the compounded 3D image can be achieved by adapting the articulated fetal model applied to different 3D images. This is beneficial in case the plurality of 3D image frames has an assembly of the partial 3D image frames corresponding to the volumetric region, which includes a portion of the fetus. In this case the fetal segmentation unit detects, these partial frames and adapts the articulated model for the partial frames based on the portion (anatomy) of the fetus included in this frame.

Figure 8A:
FIG. 8A-B shows representative medical images of fetus with identified anchor landmarks.
Figure 8B:
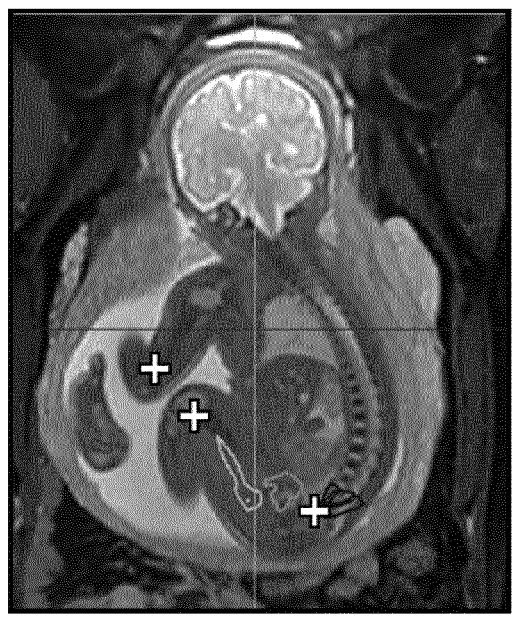
Figure 9:
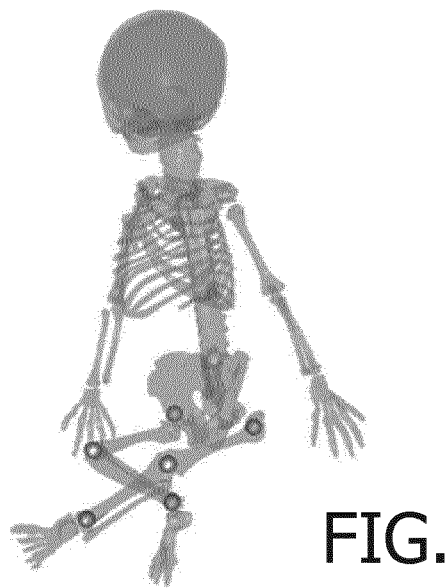
FIG. 9 illustrates a reference orientation model of the fetus displayed to the user.

In this embodiment, the articulated model adaptation comprises finding the overall constellation (for all joints the correct set of parameters such as rotation angels) to fit the model to the anatomy information acquired by the partial image. One possibility to adapt the model is by providing the user (via the user interface 20) to manually identify anchor landmarks in the image, e.g., the joint pivot. This landmark is further used as an input for segmentation unit 34 for the adaptation of the articulated fetal model for each specific. An example of the articulated model adaptation is shown for a magnetic resonance image in FIGS. 8A and 8B. These FIGs illustrate the adaptation of the constellation model to anchor landmarks. These landmarks (crosses) can be either manually or automatically identified. By adapting the model to the landmarks, the overall configuration illustrated in FIG. 9 is found.

With the prior knowledge captured in the articulated model, it is furthermore possible to adapt the model even if some landmarks are set incorrectly/missing by assuring that the determined configuration is consistent with the model. Similar workflow can be performed for the articulated model adaptation used in the partial 3D images.

The model adaption can be done in several depending on the exact given problem. For example, there can be multiple landmarks detected per limb, landmarks can be labelled or un-labelled (i.e. it is known to which anatomical structure the landmark belongs to) or the detected landmarks can have a probability how likely it is that this landmark belongs to an anatomical structure. Independent of the exact problem, adaptation will be performed in a hierarchical manner. Starting from a root, adaptation is carried out consecutively per limb and in each step a transformation is estimated so that the current limb matches to the found landmarks. Again, for the estimation of the transformation various possibilities exist, e.g., finding a closed-form solution of a sum of squared distance between landmark being defined in the limb and corresponding target landmarks or iterative optimization.

The compounded 3D image may be displayed together with the articulated fetal model used for its compounding of the fetus. Alternatively, the compounded 3D image may be displayed together with the volume rendered fetal image. The articulated fetal model (or rendered volume image) can be either shown in a separate window next the compounded 3D image; or interposed on to the compounded 3D image. This way the user may get a better spatial feeling of the fetal position and its orientation with respect to the probe.

The display further visualizes a confidence value distribution within different regions of said compounded 3D image. The confidence value distribution can be, for example, given by color indications, wherein a color scale would change from red, corresponding to regions being compounded by 3D images with lower confidence values, to green, corresponding to the regions being compounded by 3D images with higher confidence values. The user is given an opportunity to visually evaluate an overall compounded 3D image. The user can always decide to perform a new 3D frame acquisition, if a specific region in the compounded image was compounded based on the image with a low confidence value.

Figure 10:
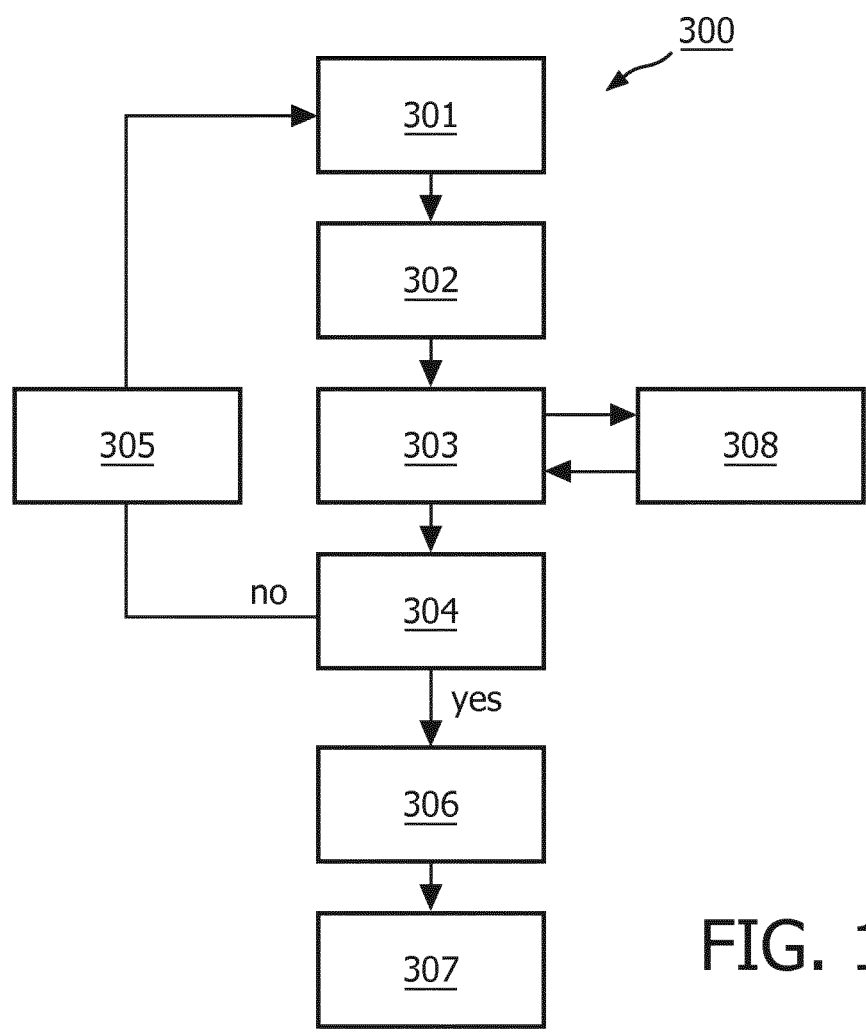
FIG. 10 a workflow diagram of the method according to the present invention.

In FIG. 10 a workflow diagram of the method 300 according to the present invention is illustrated. In step 301 a plurality of 3D ultrasound image frames of the volumetric region comprising fetus is acquired; alternatively the ultrasound system may receive the plurality of 3D ultrasound image frames via the input. Each 3D ultrasound image frame is acquired at a different look direction with respect to the fetus. In step 302 the acquired plurality of the 3D ultrasound image frames together with an articulated fetal model with a common fetal structure are stored in a compound image memory 32. In step 303 a segmentation of each 3D image frame based on the articulated fetal model is performed. In this step a plurality of 3D images of the volumetric region with an identified relative orientation of the fetus with respect to the look direction of the segmented image is performed. Additionally to segmentation a detection of a variation of the common fetal structure of a 3D frame compared to another 3D image frame of the plurality is performed in step 308, further in this step the articulated model used for each partial frame can be adapted based on the portion of the fetus anatomy included in said frame.

In step 304 the system determines an overall confidence value based on the articulated fetal model. The overall confidence value is being compared to an image compounding threshold. If the overall value is being below the image compounding threshold, in step 305 the system gives a feedback to the user informing on the fact that low quality 3D frames for a purpose of 3D image compounding were acquired. At this stage the user can decide to repeat the sequence of steps from the beginning. If the overall value is being above the image compounding threshold, in step 306 the system may weight and register each of the 3D images with respect to the common fetal structure.

And finally in step 307 a spatially compounded 3D image of the fetus is provided. In this spatially compounded 3D image different regions are formed based on contributions from the plurality of 3D images. In case the step 306 is performed the spatially compounded 3D image of the fetus would include a formation of different regions of said compounded 3D image based on weighted contributions from the 3D images determined in step 306.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An ultrasound imaging system for producing a spatially compounded image of a fetus comprising:
    an input for receiving a plurality of three dimensional (3D) ultrasound image frames of a volumetric region comprising the fetus, wherein each 3D ultrasound image frame is acquired at a different look direction with respect to the fetus by means of an ultrasound probe; and
    an ultrasound image processor responsive to the plurality of 3D ultrasound image frames, said processor arranged to:
        store the acquired plurality of 3D ultrasound image frames and an articulated fetal model, wherein the articulated fetal model includes a common fetal structure and at least one joint-limb relationship,
        segment each 3D image frame based on the articulated fetal model, wherein the ultrasound image processor is further arranged to adapt the articulated fetal model applied to a 3D image frame from the plurality, when a variation of the common fetal structure compared to another 3D image frame of the plurality is detected, wherein the ultrasound image processor is arranged to adapt the articulated fetal model by varying a joint-limb relationship of the common fetal structure,
        provide a plurality of 3D images of the volumetric region with an identified relative orientation of the fetus with respect to the look direction of the segmented image, and
        analyze, based on the articulated fetal model, an overall confidence value of the plurality of the 3D images, said image quality analyzer is further arranged to compare the overall confidence value with an image compounding threshold.

2. The ultrasound imaging system of claim 1 further comprising
    a spatial image combiner arranged to provide, when the overall confidence value is above the image compounding threshold, a spatially compounded 3D image of the fetus, wherein different regions of said compounded 3D image are formed based on contributions from the plurality of 3D images.

3. The ultrasound imaging system of claim 2, wherein the overall confidence value includes a spatial combination of confidence values, each confidence value corresponding to a 3D image from the plurality of the 3D images; and
    the spatial image combiner arranged to provide the spatially compounded 3D image of the fetus, wherein different regions of said compounded 3D image are weighted on the basis of the different confidence values of the 3D images from the plurality of 3D images.

4. The ultrasound imaging system of claim 1 further comprising a user interface coupled to the ultrasound image processor and responsive to a user manual selection of a diagnostic protocol; and
    wherein the ultrasound image processor is further arranged to analyze, based on the articulated fetal model and the selected diagnostic protocol, an overall confidence value of the plurality of the 3D images, said image quality analyzer is further arranged to compare the overall confidence value with an image compounding threshold.

5. The ultrasound imaging system of claim 1, wherein the plurality of 3D ultrasound image frames further comprises an assembly of partial 3D image frames, each partial 3D image frame corresponding to the volumetric region, which includes a portion of the fetus.

6. The ultrasound imaging system of claim 5, wherein the ultrasound image processor is arranged to adapt the articulated fetal model applied to a partial 3D image frame based on the portion of the fetus included in the respective frame.

7. The ultrasound imaging system of claim 1, wherein varying the joint-limb relationship comprises varying at least one joint pivot location and at least one limb angle value related to said pivot location.

8. The ultrasound imaging system of claim 6, further comprising a user interface coupled to the ultrasound image processor and responsive to user manual identification of at least one anchor landmark in the 3D image frame, said user interface is arranged to provide the identified location of the anchor landmark, such as joint pivot, within the 3D image frame as an input for the adaptation of the articulated fetal model.

9. The ultrasound imaging system of claim 3, wherein the articulated model comprises a set of fetal articulations, wherein each fetal articulation corresponds to a given fetal pose; and
    the ultrasound image processor is arranged to detect the variation of the common fetal structure based on the fetal pose change occurring during the acquisition of the plurality of three dimensional (3D) ultrasound image frames.

10. The ultrasound imaging system of claim 9, wherein the image quality analyzer is arranged to determine confidence values of the 3D images, which originate from 3D frames segmented with the same fetal articulation, being relatively higher with respect to confidence values corresponding to 3D images, which originate from 3D frames segmented with a different fetal articulation.

11. The ultrasound imaging system of claim 1, further comprising a display operated to give a user feedback, when the overall confidence value is below the image compounding threshold.

12. The ultrasound imaging system of claim 2, further comprising a display operated to display the compounded 3D image and the articulated fetal model with respect to the volumetric region.

13. The ultrasound imaging system of claim 2, further comprising:
    a display arranged to display the spatially compounded 3D image; and
    a user interface coupled to the ultrasound image processor, said user interface arranged to enable the user to perform biometry measurements of the fetus based on the displayed spatially compounded 3D image.

14. The ultrasound imaging system of claim 1 further comprising the ultrasound probe coupled to the input, said probe having an ultrasound transducer array operable to acquire the plurality of three dimensional (3D) ultrasound image frames of a volumetric region comprising the fetus.

15. A medical imaging method for inspecting a volumetric region comprising fetus is provided comprising the steps of:
    receiving a plurality of three dimensional (3D) ultrasound image frames of a volumetric region with the fetus, wherein each 3D ultrasound image frame is acquired at a different look direction with respect to the fetus, by an ultrasound probe, storing the acquired plurality of the 3D ultrasound image frames and an articulated fetal model with a common fetal structure, wherein the articulated fetal model includes a common fetal structure and at least one joint-limb relationship, segmenting each 3D image frame based on the articulated fetal model;

adapting the articulated fetal model applied to a 3D image frame, when a variation of the common fetal structure compared to another 3D image frame of the plurality is detected, wherein the ultrasound image processor is arranged to adapt the articulated fetal model by varying a joint-limb relationship of the common fetal structure;

providing a plurality of 3D images of the volumetric region with an identified relative orientation of the fetus with respect to the look direction of the segmented image, providing a spatially compounded 3D image of the fetus, wherein different regions of said compounded 3D image are formed based on contributions from the plurality of 3D images.

16. The method of claim 14, further comprising:

weighting and registering each of the 3D images with respect to the common fetal structure, wherein providing the spatially compounded 3D image of the fetus, includes a formation of different regions of said compounded 3D image based on weighted contributions from the 3D images of the plurality of 3D images.

* * * * *